(12) United States Patent
Naimark et al.

(10) Patent No.: US 6,893,431 B2
(45) Date of Patent: May 17, 2005

(54) MEDICAL DEVICE FOR DELIVERING PATCHES

(75) Inventors: Wendy Naimark, Cambridge, MA (US); Maria Palasis, Wellesley, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 152 days.

(21) Appl. No.: 09/977,758

(22) Filed: Oct. 15, 2001

(65) Prior Publication Data

US 2003/0073979 A1 Apr. 17, 2003

(51) Int. Cl.⁷ .............................. A61M 3/00
(52) U.S. Cl. .................... 604/891.1; 606/213
(58) Field of Search .............. 604/891.1, 93.01, 604/96.01, 104–109; 600/201, 204, 207; 606/192–198, 159, 127, 114, 213, 151

(56) References Cited

U.S. PATENT DOCUMENTS

| | | |
|---|---|---|
| 4,051,840 A | 10/1977 | Kantrowitz et al. |
| 4,164,045 A | 8/1979 | Bokros et al. |
| 4,577,631 A * | 3/1986 | Kreamer ............ 606/108 |
| 4,915,694 A | 4/1990 | Yamamoto et al. |
| 5,002,560 A | 3/1991 | Machold et al. |
| 5,030,195 A | 7/1991 | Nardi |
| 5,053,008 A | 10/1991 | Bajaj |
| 5,263,963 A | 11/1993 | Garrison et al. |
| 5,327,913 A | 7/1994 | Taheri |
| 5,354,279 A | 10/1994 | Höfling |
| 5,385,156 A | 1/1995 | Oliva |
| 5,429,634 A | 7/1995 | Narciso, Jr. |
| 5,562,726 A | 10/1996 | Chuter |
| 5,593,405 A | 1/1997 | Osypka |
| 5,624,946 A | 4/1997 | Williams |
| 5,647,870 A | 7/1997 | Kordis et al. |
| 5,662,671 A | 9/1997 | Barbut et al. |
| 5,693,085 A * | 12/1997 | Buirge et al. ............ 623/1.13 |
| 5,713,863 A | 2/1998 | Vigil et al. |
| 5,720,776 A | 2/1998 | Chuter et al. |
| 5,725,525 A | 3/1998 | Kordis |
| 5,755,777 A | 5/1998 | Chuter |
| 5,814,079 A | 9/1998 | Kieval |
| 5,824,065 A | 10/1998 | Gross |
| 5,829,447 A | 11/1998 | Stevens et al. |
| 5,843,472 A | 12/1998 | Ma et al. |
| 5,855,614 A | 1/1999 | Stevens et al. |
| 5,895,399 A | 4/1999 | Barbut et al. |
| 5,928,943 A | 7/1999 | Franz et al. |
| 6,001,118 A | 12/1999 | Daniel et al. |
| 6,039,967 A | 3/2000 | Ottoboni et al. |
| 6,045,565 A | 4/2000 | Ellis et al. |
| 6,053,932 A | 4/2000 | Daniel et al. |
| 6,076,013 A | 6/2000 | Brennan et al. |
| 6,119,030 A | 9/2000 | Morency |
| 6,391,052 B2 * | 5/2002 | Buirge et al. ............ 623/1.47 |

FOREIGN PATENT DOCUMENTS

| | | |
|---|---|---|
| WO | WO 99/22655 | 5/1999 |
| WO | WO 99/64580 | 12/1999 |

* cited by examiner

*Primary Examiner*—Kevin C. Sirmons
(74) *Attorney, Agent, or Firm*—Jones Day

(57) ABSTRACT

The present invention relates to a medical device and method for treating the body tissue of a patient. The present invention is also directed to a method of making the medical device and a method of using the medical device. More particularly, the invention relates to a medical device which is inserted into the body for delivery of therapeutic patches to the surface of a body lumen, organ or cavity. Specifically, the medical device has an umbrella-like or a basket-like expandable assembly; and a therapeutic patch. The expandable assembly is capable of changing from a retracted position to an expanded position. The expandable assembly can be self-expanding or non-self-expanding. In one embodiment, the medical device comprises an elongated member; an umbrella-like expandable assembly which has a plurality of wire elements; and a therapeutic patch. The therapeutic patch comprises a sheet having two opposing surfaces wherein one of the surface comprises an adhesive material and at least one biologically active material.

21 Claims, 9 Drawing Sheets

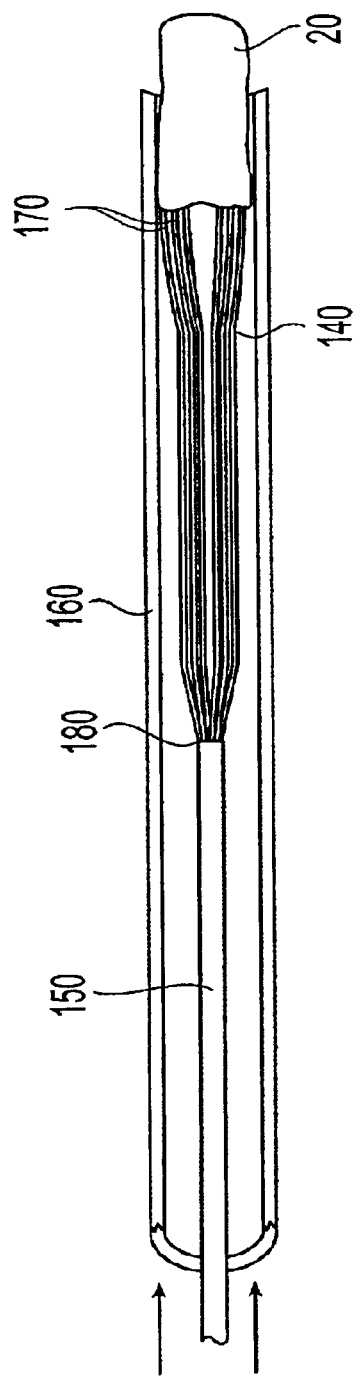
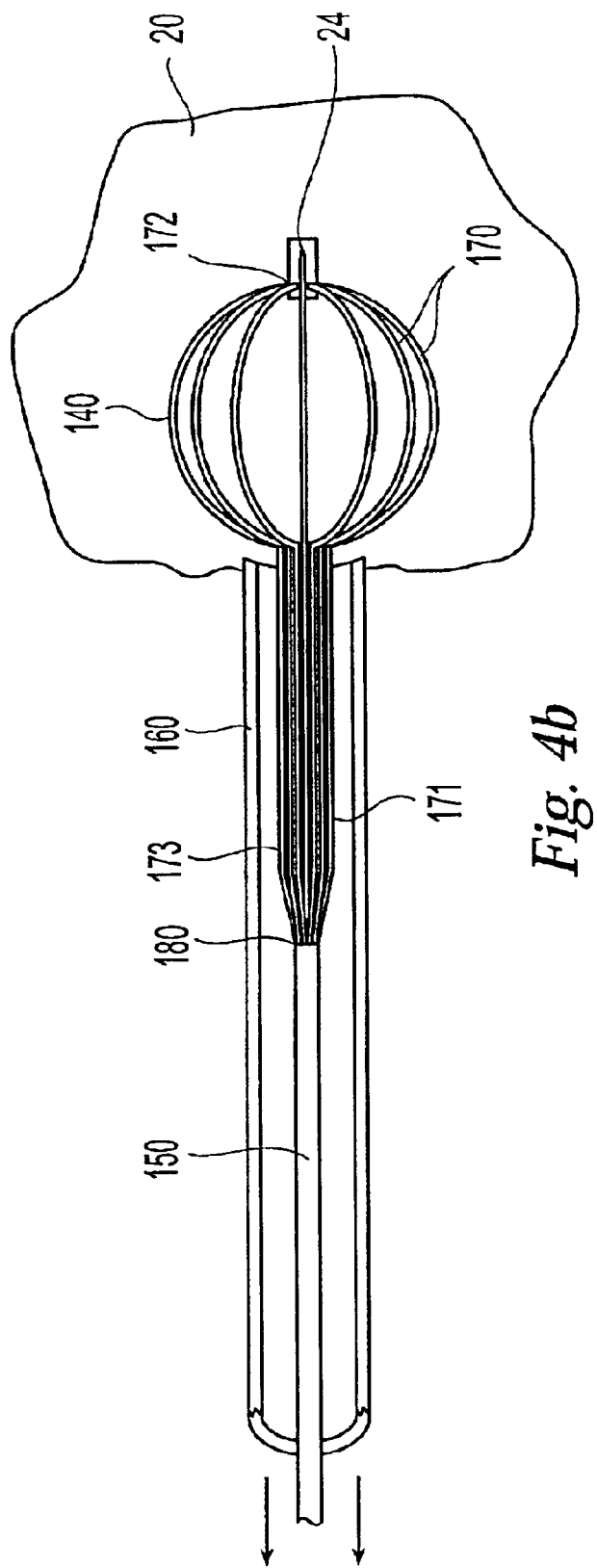

MEDICAL DEVICE FOR DELIVERING PATCHES

1. FIELD OF THE INVENTION

The present invention generally relates to a medical device which is inserted or implanted into the body for delivery of a patch to the surface of a body lumen or an internal body cavity or organ. More particularly, the invention is directed to a medical device that comprises an expandable assembly and a therapeutic patch attached thereon. The medical device enables the administration of a biologically active material on a solid support to the surface of a body lumen or internal body cavity or organ.

2. BACKGROUND OF THE INVENTION

Heart failure affects approximately three million Americans, and new cases of heart failure number about 400,000 each year. Congestive heart failure (CHF) is particularly insidious, affecting at least two million Americans, and is a syndrome characterized by left ventricular dysfunction, reduced exercise tolerance, impaired quality of life, and markedly shortened life expectancy. In patients suffering from CHF, decreased contractility of the left ventricle leads to reduced cardiac output with consequent systemic arterial and venous vasoconstriction. This vasoconstriction, which promotes the vicious cycle of further reductions of stroke volume is followed by an increased elevation of vascular resistance. A number of techniques are available for treating cardiovascular disease such as cardiovascular by-pass surgery, coronary angioplasty, laser angioplasty and atherectomy. These techniques are generally applied to by-pass or open lesions in coronary vessels to restore and increase blood flow to the heart muscle. In some patients, the number of lesions are so great, or the location so remote in the patient vasculature that restoring blood flow to the heart muscle is difficult.

However, despite these efforts, the degree of clinical efficacy has been limited. Improvement in functional capacity and exercise time is small and mortality, although reduced, continues to be high. Thus, there remains a long felt, yet currently unmet need to provide a therapeutic solution to minimize the deterioration of the heart associated with CHF.

The prior art method of delivering therapeutics using needle injection is problematic because such treatment is too localized. Also there are problems associated with patch delivery whereby a biologically active material is incorporated into a patch. Patch delivery provides a means of localizing and controlling therapeutic agent release to the heart and other organs. Currently, affixing such delivery vehicles to the myocardium is only achieved with maximally invasive surgical techniques (i.e. open-heart surgery). Hence, direct exposure of the heart is necessary for patch attachment. Clearly, there remains a great need for a medical device which delivers therapeutic agents that is minimally invasive. With the device as described in the present invention, patch delivery can be accomplished using a minimally invasive catheter-based delivery system.

3. SUMMARY OF THE INVENTION

The present invention is based upon the observation of the inventors that a therapeutic patch may be delivered to the site of treatment, usually a body lumen or an internal body cavity or organ, by means of a catheter-based patch deployment-delivery system. The present medical device addresses four shortcomings of the current technology. First, with the advent of a catheter-based delivery system, patch deployment is no longer limited to maximally invasive surgical procedures. Second, biologically active materials released from a solid support, i.e., patch delivery, eliminates the systemic leakage routinely encountered with solution formulations. Third, a patch system serves as a network bridge that provides adequate surface coverage to bridge healthy and ischemic tissue thereby reuniting healthy and injured tissue, and re-establishing a continuous functional tissue network. From the standpoint of gene therapy, patch delivery will resolve a key downfall of current strategies where injection of cells, genes, or drugs into the injured area may result in isolated areas of regeneration. Fourth, the catheter-based patch deployment patch delivery system allows for minimally invasive delivery to a large area of treatment such as a surface of the myocardium.

It is an object of this invention to deliver a therapeutic patch which is non-thrombogenic, minimally inflammatory and generally well received and well tolerated by the human body, to the surface of a body lumen or an internal body cavity or organ.

It is also an object of this invention to provide a medical device for treating the body tissue of a patient. The medical device comprises an elongated member having a proximal end and a distal end; an expandable assembly disposed at the distal end of the elongated member, wherein the expandable assembly is capable of changing from a retracted position to an expanded position and the expandable assembly comprises a plurality of wire elements and wherein each wire element has two opposing ends; and a patch having two opposing surfaces; wherein one of the opposing surfaces comprises an adhesive material and the biologically active material; and wherein the other opposing surface is disposed upon at least one of the wire elements. The expandable assembly can be non-self-expandable or self-expandable.

While it will be appreciated that the expandable assembly can be arranged in a wide variety of configurations, in preferred embodiments, the expandable assembly takes on an umbrella-like or a basket-like configuration. In one embodiment, the expandable patch delivery assembly has an umbrella-like configuration when the assembly is expanded. The medical device comprises an elongated member having a proximal end and a distal end which defines a longitudinal axis; an umbrella-like expandable assembly comprising a plurality of wire elements, each having two opposing ends. The elongated member may be further connected at its proximal end to a catheter body. In one embodiment, the umbrella-like expandable patch delivery assembly is non-self expanding and comprises an expansion mechanism for expanding the expandable assembly. The expansion mechanism comprises a plunger having a lumen being sized to slidably receive a portion of the elongated member therein. The patch comprises two opposing surfaces. One of the surfaces comprises at least one biologically active material and an adhesive. The other opposing surface is disposed on the plurality of wire elements of the umbrella-like expandable assembly. The patch changes from a retracted position to an expanded position when the expandable assembly changes from a retracted position to an expanded position as the plunger slides along the elongated member. In one embodiment, one end of at least one wire element is connected to the distal end of the elongated member at a flexible joint. In another embodiment, one end of at least one wire element is flexibly connected to the plunger.

In another embodiment, the umbrella-like expandable assembly is self expanding. In its rest position, the umbrella-like self-expandable assembly is in its expanded position. A guide sheath which is sized to slidably receive the elongated member and the umbrella-like self-expandable assembly is placed around the umbrella-like self-expandable assembly to keep the assembly in its retracted position. Once the guide sheath is removed, the umbrella-like self-expandable assembly returns to its expanded position.

Another embodiment of the medical device of the present invention comprises an expandable patch delivery assembly which has a basket-like configuration when the assembly is expanded. The medical device comprises an elongated member, which has a proximal end and a distal end which defines a longitudinal axis. An expandable assembly, comprised of a plurality of wire elements, is attached to the distal end of the elongated member. Each wire element has two opposing ends. In one embodiment, the basket-like expandable assembly is non-self expanding and further comprises an expansion mechanism. The expansion mechanism comprises a plunger having a lumen being sized to slidably receive a portion of the elongated member therein. In a specific embodiment, one end of at least one wire element is flexibly connected to the plunger.

In another embodiment, the basket-like expandable assembly is self-expanding. Both ends of at least one wire element is connected to the distal end of the elongated member. There is a midpoint between the opposing ends of each wire element. The midpoints of at least two wire elements can intersect and can be connected to each other at a hub. In another embodiment, one end of at least one wire element is connected to the distal end of the elongated member and the other end of at least one wire element is connect to the distal end of the elongated member at a point more distal than the other end of the wire element. A guide sheath having a lumen is sized to slidably receive the basket-like self-expandable assembly. When the guide sheath slides along the longitudinal axis, the basket-like expandable assembly expands and retracts. A patch having opposing surfaces is disposed on the basket-like expandable assembly. One of the surfaces comprises a biologically active material and an adhesive material. The other opposing surface is disposed onto the wire elements of the basket-like expandable assembly. The patch is changed from a retracted position to an expanded position as the expandable assembly retracts and expands.

The present invention is also directed to a method for treating the body tissue of a patient. The method comprises inserting any of the above-described medical device into the patient's body in a manner such that the expandable assembly is proximal to the body tissue surface being treated. The expandable assembly is expanded from a retracted position to an expanded position and contacting the body tissue that needs to be treated with the surface of the patch comprising the biologically active material.

Furthermore, it is an object of the present invention to provide a method of making a medical device of the present invention for treating body tissue of a patient. The method of making a medical device for treating the surface of a body tissue of a patient comprises disposing the expandable assembly upon the distal end of the elongated member and disposing the patch onto at least one wire element of the expandable assembly. In an embodiment, the patch is disposed upon the wire element by loosely wrapping the surface of the patch that is without the biologically active material on the wire element.

In a preferred embodiment, the patch is circular in shape and has holes at the periphery which can be secured onto hooks that are disposed on the wire elements of the expandable assembly. In another embodiment, a water soluble glue is used to secure the patch onto the expandable assembly.

4. BRIEF DESCRIPTION OF THE DRAWINGS

The various advantages and novel features of this invention will be more fully apparent from a reading of the detailed description of the present invention in conjunction with the accompanying drawings in which like reference numerals refer to like parts.

Figure 2A:
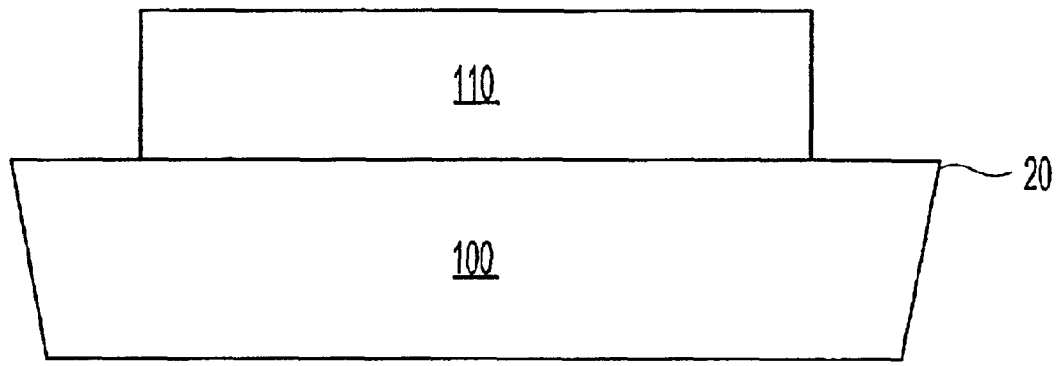

FIG. 2a illustrates a schematic diagram of a therapeutic patch 20 with two-opposing surfaces 100 and 110.

Figure 2B:
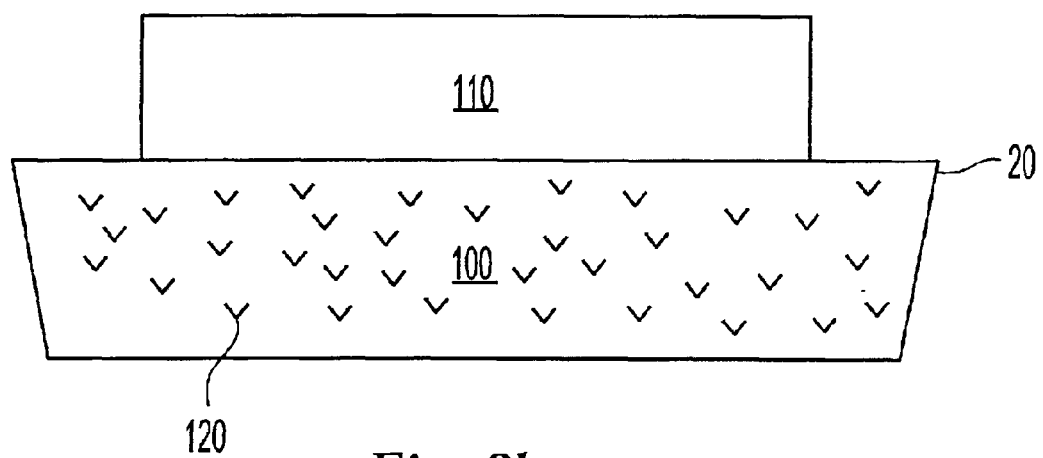

FIG. 2b illustrates a schematic diagram of a therapeutic patch 20 with two-opposing surfaces 100 and 110. Surface 100 has a plurality of micro-needles 120.

Figure 3:
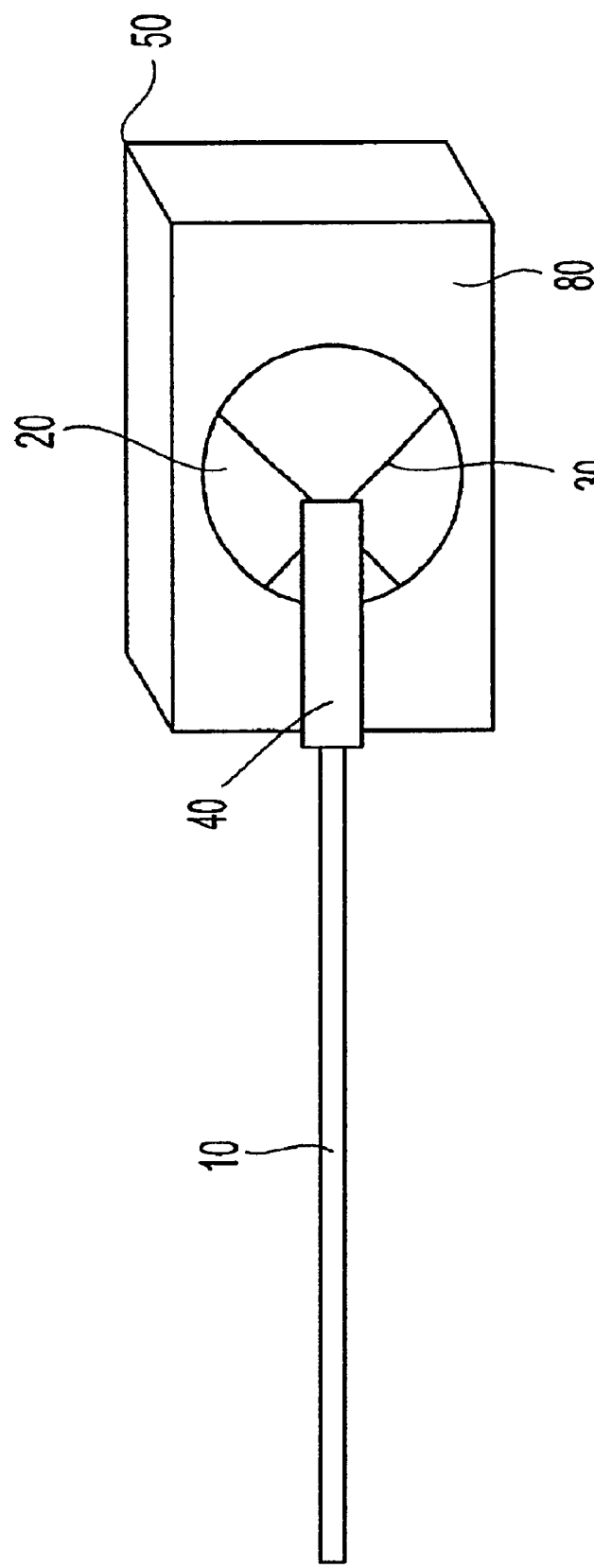

FIG. 3 illustrates a schematic diagram showing a deployed patch 20 adhering onto the surface of the myocardium 80.

FIG. 4a illustrates an embodiment of the medical device having a basket-like expandable assembly 140 wherein the assembly is in its retracted position.

FIG. 4b illustrates the same medical device as in FIG. 4a in which the basket-like expandable assembly 140 is expanded to deliver a therapeutic patch 20.

5. DETAILED DESCRIPTION OF THE INVENTION

5.1 The Apparatus of the Invention

In general, this invention is directed to a medical device which can deliver a therapeutic patch to a surface of a body lumen or an internal organ with minimum invasive surgery. The medical device of the present invention comprises an elongated member; an expandable assembly; and a therapeutic patch.

In one embodiment, the medical device comprises an expandable assembly with an umbrella-like configuration and a therapeutic patch. The umbrella-like expandable assembly comprises a plurality of wire elements each having two opposing ends and the umbrella-like expandable assembly may be movable between an expanded position and a retracted position. The umbrella-like expandable assembly is disposed on the distal end of an elongated member. The umbrella-like expandable assembly can be non-self expanding. In such an embodiment, expansion is controlled through an expansion mechanism such as a plunger. The plunger has a lumen that is being sized to slidably adapt to the elongated member. The wire elements can be made of flexible, resilient wires from materials such as nickel-titanium alloys (Nitinol™), stainless steel, platinum or other material exhibiting similar super-elastic characteristics. A therapeutic patch is disposed onto the plurality of wire elements of the umbrella-like expandable assembly. The material that can be used to make the patch may be biocompatible material such as polyester or polytetrafluoroethylene, or a portion of the patient's pericardium or other natural body membrane. Biologically active materials can be secured onto the therapeutic patch using an adhesive material such as a bioadhesive or formulated into the patch. The adhesive material is also used to provide adhesion for the therapeutic patch to adhere onto the surface of the body tissue that requires treatment once the umbrella-like expandable assembly of the medical device is deployed.

Figure 1A:
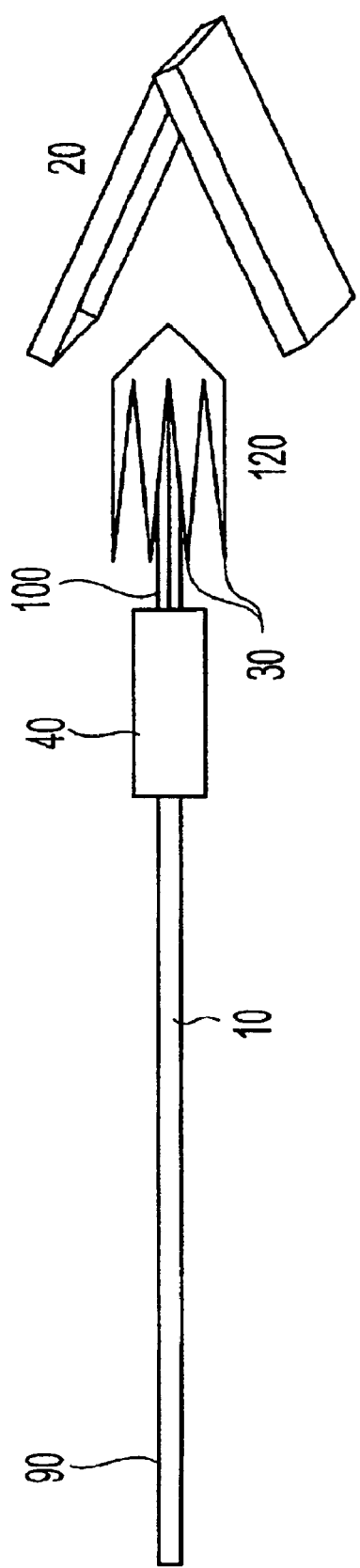
FIG. 1a illustrates a schematic diagram showing the various parts of an embodiment of a medical device having an expandable assembly having an umbrella-like configuration.

FIG. 1a illustrates one embodiment of the umbrella-like expandable assembly that can be used in the medical device of the present invention. This embodiment includes an umbrella-like assembly 120 having an expandable therapeutic patch 20 disposed thereon. The medical device comprises an elongated member 10 with a sliding plunger or expansion mechanism 40. The elongated member 10 has a proximal 90 and a distal end 100. The umbrella-like expandable assembly 120 comprises a plurality of wire elements 30. Each of the wire elements 30 has a proximal end and a distal end. The proximal ends of the wire elements are connected to the distal end of the elongated member 10 at a flexible joint (not shown). A therapeutic patch 20 is disposed onto the wire elements 30 of the umbrella-like expandable assembly 120.

As shown in FIG. 1a and in more detail in FIGS. 2a and b, the therapeutic patch 20 comprises a sheet having opposing surfaces 100 and 110. One of the opposing surfaces 100 comprises an adhesive material and at least one biologically active material. The other opposing surface 110 is disposed onto the plurality of wire elements 30. As shown in FIG. 2b, the opposing surface comprising the biologically active material can have a plurality of micro-needles for facilitating delivery of the biologically active material. The patch 20 may be wrapped onto the wire elements 30 of the umbrella-like expandable assembly like an accordion or in an S-shaped form similar to a collapsed balloon. Alternatively, the patch can be attached to hooks disposed on at least one wire element.

The patch 20 is movable between an expanded position and a retracted position in concert with the expandable assembly as the expansion mechanism or plunger 40 slides along the elongated member 10. Specifically the slidable plunger or expansion mechanism 40 has a lumen that is sized to slidably receive a portion of the elongated member 10 therein. When expansion mechanism or plunger 40 is pushed along the elongated member 10 toward the umbrella-like expandable assembly 120, the plunger pushes the wire elements 30 and causes patch 20 to expand outwardly from the wire elements and places patch 20 into the deployed position as shown in FIGS. 1b and 3.

Figure 1B:
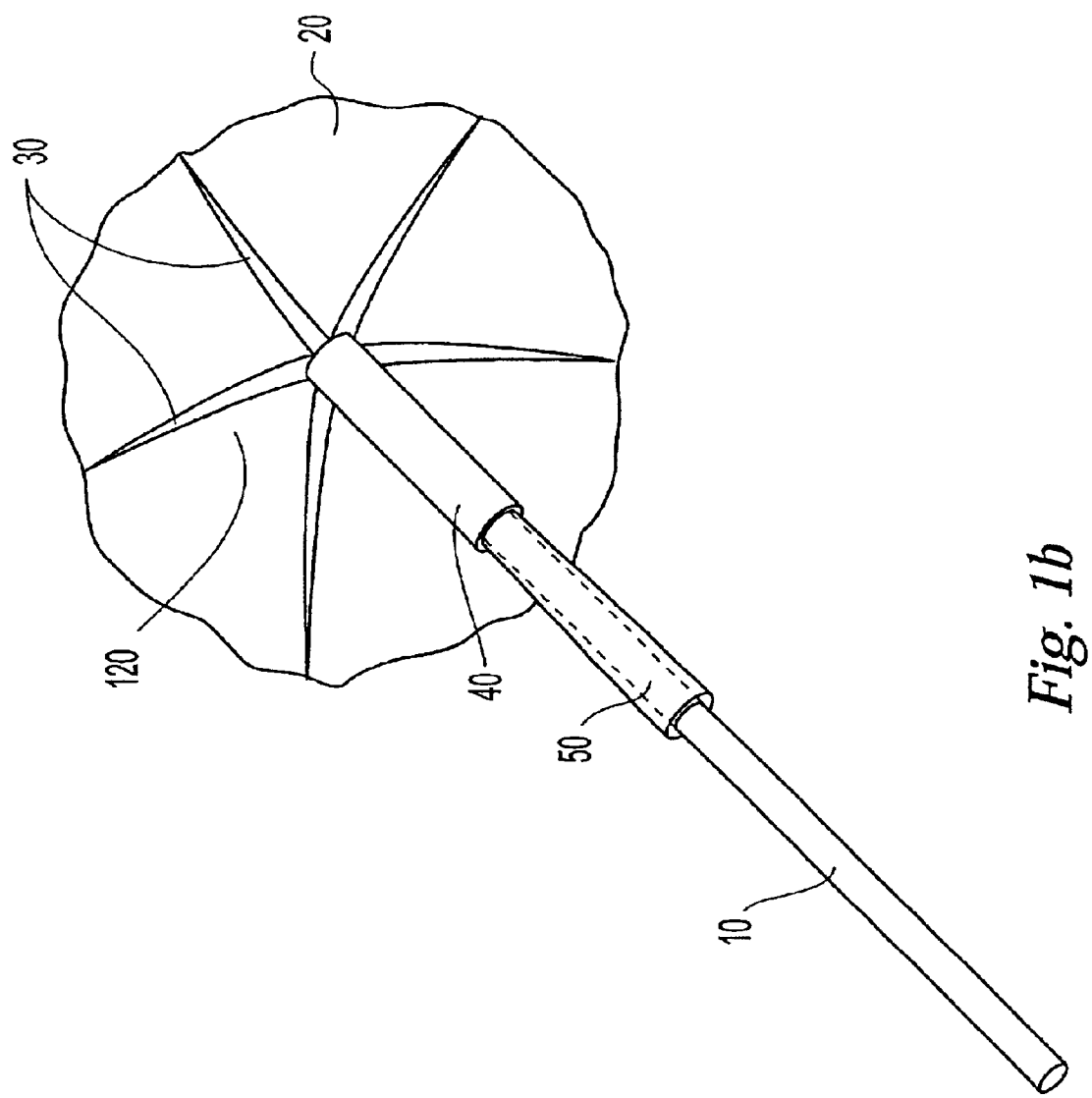
FIG. 1b illustrates a medical device with an expandable assembly having an umbrella-like configuration as showing in FIG. 1a in its expanded position.

FIG. 1b illustrates the medical device as shown in FIG. 1a with the umbrella-like expandable assembly in the expanded position. The plunger 40 pushes the wire elements 30 to diverge from one another. Patch 20, which is disposed on the wire elements, is brought to an expanded position. Also, the proximal end of the plunger 40 can be affixed to a slideable shaft 50 that is threaded over the elongated member 10 as shown in FIG. 1b. The slideable shaft 50 can be mechanically manipulated to move the plunger 40 backward and forward to expand and collapse the expandable assemble 120. Alternatively, the plunger 40 may be advanced distally over at least a portion of the wire elements 30 to collapse the wire elements 30 so that they resemble the ribs of an overturned umbrella.

Figure 1C:
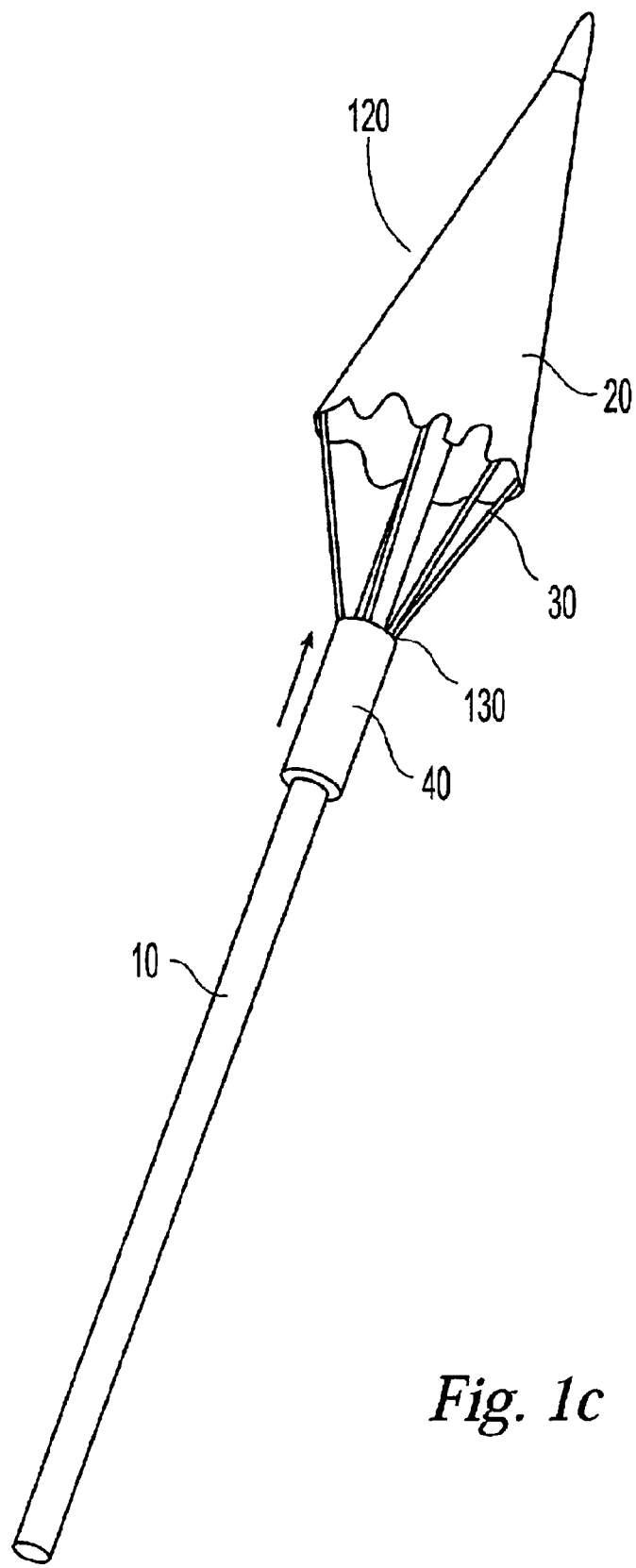
FIG. 1c illustrates a schematic diagram showing an embodiment of a medical device having an expandable assembly with an umbrella-like configuration.
Figure 1D:
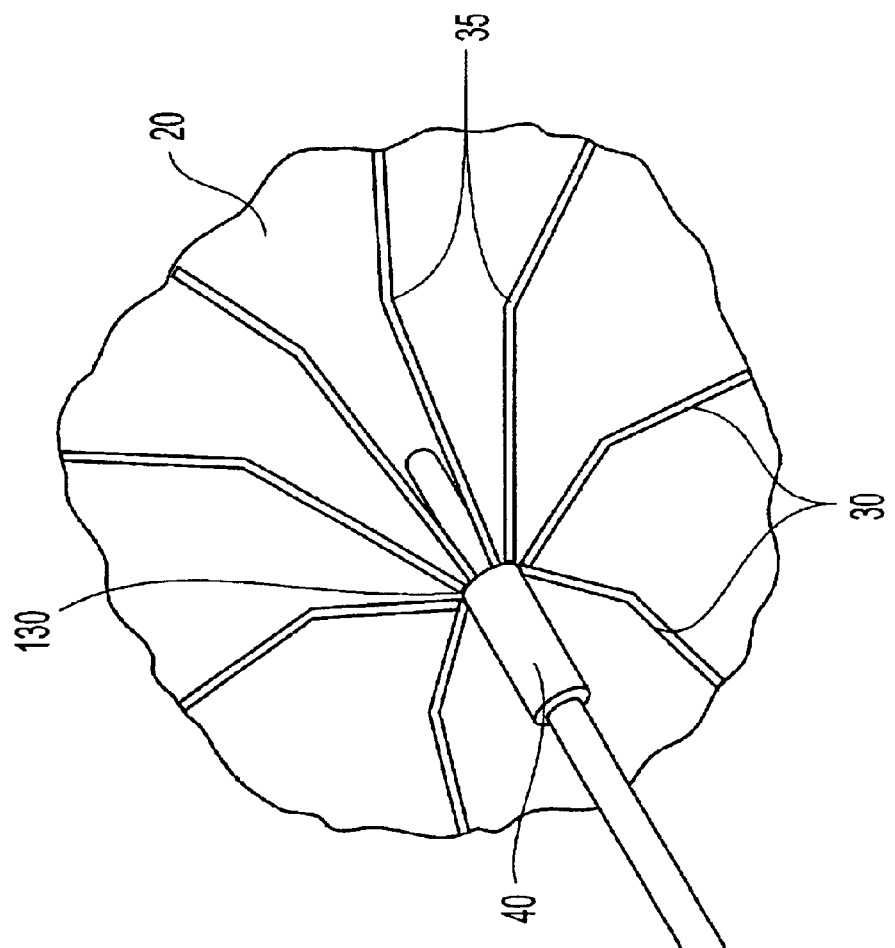
FIG 1d illustrates a medical device with an expandable assembly having an umbrella-like configuration as shown in FIG. 1c in its expanded position.

FIG. 1c depicts another embodiment of the umbrella-like expandable assembly 120 with a therapeutic patch 20. In this embodiment, the proximal ends of each of the wire elements 30 are connected to the distal end of the plunger or expansion mechanism 40 at a flexible joint 130. In such a configuration, when the plunger or expansion mechanism 40 slides distally along the elongated member 10, the wire elements 30 are pushed distally to expand the umbrella-like expandable assembly 120. The wire elements diverge from one another as shown in FIG. 1d. Accordingly, the therapeutic patch 20 which is disposed on the wire elements expands and is delivered to the body tissue.

FIG. 1d illustrates the medical device as shown in FIG. 1c in its expanded position. One end of the wire element 30 is flexibly joined 130 to the plunger or expansion mechanism 40. In one embodiment, the wire element 30 may be able to bend at a point 35 between the two ends of the wire element 30. When the plunger or expansion mechanism 40 advances distally along the elongated member 10, the wire elements 30 diverge from one another. Accordingly, the expandable assembly 120 expands, causing the patch 20 to expand.

Figure 1E:
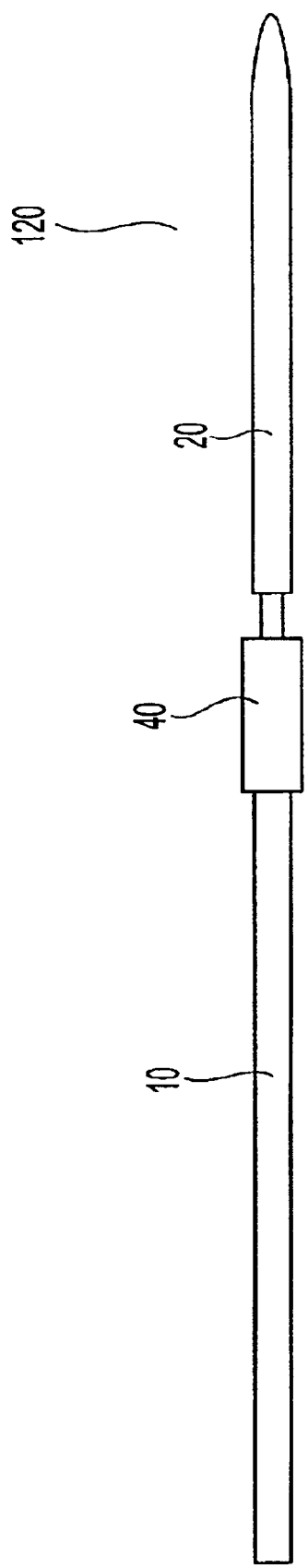
FIG. 1e illustrates a schematic diagram of a medical device with a sliding plunger 40 in which its expandable assembly is in its retracted position and the patch 20 is in a retracted position.

FIG. 1e illustrates the medical device with the umbrella-like expandable assembly in a retracted position. Preferably, when the umbrella-like expandable assembly is retracted, it collapses to approximate the outer diameter of the elongated member 10.

Figure 1F:
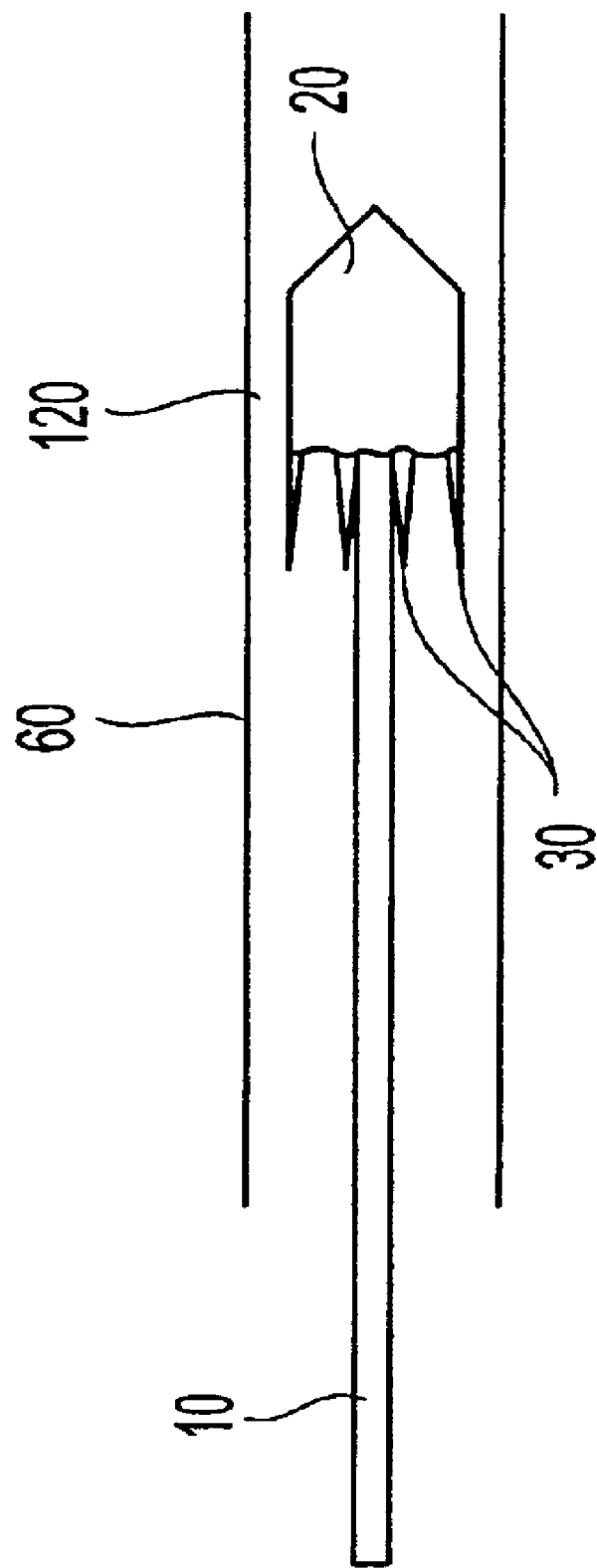
FIG. 1f illustrates a schematic diagram of a medical device having a self-expanding expandable assembly in its retracted position.

In another embodiment of the medical device, the umbrella-like expandable assembly 120 comprising wire elements 30, can be self-expanding as shown in FIG. 1f. More specifically, in its rest state or position the expanded assembly remains expanded. The umbrella-like expandable assembly can be confined by a guide sheath 60 that holds the assembly 120 in a retracted position. When the guide sheath 60 is removed, the expandable assembly 120 returns to its expanded position to deliver the patch 20. The guide sheath 60 can be advanced toward the distal end of the device to return the expanded assembly back to a retracted position before removal of the wire.

FIG. 3 illustrates a medical device with the umbrella-like expandable assembly of the invention being used to deliver a therapeutic patch 20 to the surface of the myocardium 80. After the medical device has been positioned adjacent to the body tissue to be treated, the umbrella-like expandable assembly is expanded as discussed above. For instance, the plunger or expansion mechanism 40 slides along the elongated member 10 to push the wire elements 30 into an expanded position. When the umbrella-like expandable assembly is expanded, the surface of the therapeutic patch 20 that comprises the adhesive material and biologically active material contacts and adheres to the surface of the myocardium 80. The therapeutic patch 20 is then detached from the wire elements 30 when the umbrella-like expandable assembly retracts.

An additional component may be provided for introducing the medical device of the present invention to the target site within the treatment region that is to be treated. For example, a conventional sheath and obturator (stylet) assembly can be used to initially access the target site. The assembly can be positioned under ultrasonic or other conventional imaging, with the obturator/stylet then being removed to leave an access lumen through the sheath. The expandable assembly of any configuration can hen be introduced through the sheath lumen. In one embodiment, the wire elements of an umbrella-like expandable assembly are then extended so that the therapeutic patch can be deployed at the surface of the body tissue of a patient and the umbrella-like expandable assembly can subsequently be withdrawn.

In another embodiment, the medical device comprises a basket-like expandable assembly and a therapeutic patch. A basket-like expandable assembly comprises a plurality of wire elements in the shape of a basket secured to the distal end of an elongated member. The basket-like expandable assembly is capable of changing from a retracted position to an expanded position. The therapeutic patch is disposed on the plurality of wire elements of the basket-like expandable assembly and is expandable from a retracted position.

FIGS. 4a and 4b depict one version of the medical device with basket-like expandable assembly of the invention in which the assembly is self-expanding. In general, a basket-like expandable assembly 140 includes an elongated catheter body 150 formed by a tubular member which has a distal end and a proximal end. A basket-like expandable assembly 140 formed of a plurality of wire elements 170 is secured at the distal end 180 of the catheter body 150. In this embodiment, each wire element has a first end 171, a second end 173 and a midpoint 172. The first and second ends are attached to the distal end 180 of the catheter body or elongated member 150. The midpoint 172 of the strands are held together by a tip member 24, which is a hub. In another embodiment, one end of the wire element is attached to the distal end of the elongated member and the other end is attached to the distal end of the elongated member at a point more distal than the other end of the wire element. Preferably, the basket-like expandable assembly includes at least about three (3) wire elements although fewer wire elements may be provided. For example, preferably about four (4) to about twenty (20) wire elements may be used to form the basket-like expandable assembly.

The basket-like expandable assembly is inserted into a guide sheath 160 having a lumen being sized to slidably receive the basket-like expandable assembly and the elongated member. In particular, the guide sheath has an inner diameter that is greater than the outer diameter of the catheter body and the collapsed basket-like expandable assembly. The guide sheath controls the expansion and retraction of the basket-like expandable assembly it moves along the elongated member. As a result, the guide sheath is capable of sliding along the basket-like expandable assembly.

In addition, although a circular shape is shown, it will be appreciated that the wire elements may be arranged in a variety of curved, elliptical or other looped shapes, that may together define three-dimensional, basket-like expandable assembly. The wire elements are preferably spaced apart from one another to substantially isolate the wire elements from one another, and are preferably spaced apart evenly. Also, preferably the wire elements are of the same length.

During use, the basket-like expandable assembly is directed between retracted and expanded conditions. In particular, the wire elements with the therapeutic patch are compressed into a retracted condition for introduction into a patient's body, for example, through the cardiovascular system. The basket-like expandable assembly and the patch is deployed at a target site within the body, for example, within a heart chamber, where the guide sheath is pulled back, allowing the wire elements to return to their expanded condition for use. Upon deployment of the basket-like expandable assembly, the therapeutic patch comes in contact with the surface of the body tissue to be treated, and adheres to the surface of the body tissue. The medical device comprising the basket-like expandable assembly is retracted and removed from the treated area.

As FIG. 4a shows, movement of the slidable sheath 160 towards the distal end of the elongated member 150, moves the sheath 160 over the basket-like expandable assembly 140. In this position, the slidable sheath 160 compresses and collapses the basket-like expandable assembly 140 for introduction through a vein or artery to the intended treatment site within the body. As FIG. 4b shows, movement towards the proximal end of the elongated member 150 moves the guide sheath 160 away from the basket-like expandable assembly 140. This movement removes the compression force of the guide sheath 160 on the basket-like expandable assembly 140. The basket-like expandable assembly 140 is allowed to expand and assumes its three-dimensional basket-like shape. A therapeutic patch 20 is disposed on the wire elements 170 of the basket-like expandable assembly. When the basket-like expandable assembly is in its retracted position, the therapeutic patch is disposed around the retracted basket-like expandable assembly (not shown). When the medical device is inserted adjacent to the surface of body tissue that is to be treated, the basket-like expandable assembly is expanded by retracting the guide sheath 160 to deliver the patch 20 to the body tissue.

In another embodiment, the medical device comprises a basket-like expandable assembly that is not self-expanding. This embodiment further comprises an expansion mechanism for expanding the basket-like expandable assembly. In one embodiment, the expansion mechanism is a plunger having a lumen being sized to slidably receive a portion of the elongated member such as that used in the medical device having an umbrella-like expandable assembly described above. In an alternative embodiment one end of at least one wire element is flexibly connected to the plunger or expansion mechanism.

5.2 Suitable Therapeutic Patches

FIG. 2a illustrates a therapeutic patch that may be used in the present invention. The therapeutic patch 20 has two opposing surfaces, one surface 100 has at least one adhesive material and at least one biologically active material. The other surface 110 is disposed against the umbrella-like expandable assembly 120 as shown in FIGS. 1a and 1c, or basket-like expandable assembly as shown in FIGS. 4a and b. The patch which is non-thrombogenic, non-inflammatory, delivers relatively high doses of one or a combination of biologically active material locally to body tissue in a sustained fashion.

The patch may comprise a sheet that is made of natural polymers, synthetic polymers, metals or biological fabric. Patch 20 is preferably formed of woven or braided fibers or wires, membranes, porous or fibrous scaffolds made of a polymer. The polymer(s) useful for forming the therapeutic patch should be ones that are biocompatible and avoid irritation to body tissue. They can be either biostable or bioabsorbable. Polymers that can be used in the present invention include hydrophilic or hydrophobic ones such as polycarboxylic acids, cellulosic polymers, including cellulose acetate and cellulose nitrate, gelatin, polyvinylpyrrolidone, cross-linked polyvinylpyrrolidone, polyanhydrides including maleic anhydride polymers, polyamides, polyvinyl alcohols, copolymers of vinyl monomers such as PVA, polyvinyl ethers, polyvinyl aromatics, polyethylene oxides, glycosaminoglycans, polysaccharides, polyesters including polyethylene terephthalate, polyacrylamides, polyethers, polysulfones, polyether sulfone, polycarbonate, polyalkylenes including polypropylene, polyethylene and high molecular weight polyethylene, halogenated polyalkylenes including polytetrafluoroethylene, polyurethanes, polyorthoesters, proteins, polypeptides, silicones, siloxane polymers, polylactic acid, polyglycolic acid, polycaprolactone, polyhydroxybutyrate valerate and blends and copolymers thereof as well as other biodegradable, bioabsorbable and biostable polymers, copolymers and hydrogels.

It is preferable that the patch is made of a biodegradable material, i.e., a material capable of being absorbed by the body after it is no longer needed. However, a patch can also be made of a non-bioabsorbable such as plastic mesh, which include polypropylene mesh such as MARLEX™ and GORTEX™. The selection of the type of patch material depends on the disease or condition that is to be treated and can be determined by one skilled in the art. Biodegradable polymers suitable for use in the present invention include: poly(L-lactide) (PLLA), poly(D,L-lactide) (PLA), poly(glycolide) (PGA), poly(L-lactide-co-D,L-Lactide) (PLLA/PLA), poly(L-lactide-co-glycolide) (PLA/PGA), poly(glocolide-co-trimethylene carbonate) (PGA/PTMC), polydioxanone (PDS), polycaprolactone (PCL), polyhydroxybutyrate (PHBT), poly(phosphazenes), poly(D,L-lactide-co-caprolactone) (PLA/PCL), poly(glycoside-co-caprolactone) (PGA/PCL), poly(phosphase ester), poly(ethylene terephthalate) and polyanhydrides.

In addition, other suitable high strength, high modulus organopolymeric materials may be used. These include aromatic polyimides and aromatic polyamides, aromatic copolyamides, such as the reaction products of phenylenebis(aminobenzamide) and isophthaloyl chloride, all-aromatic polybenzimidazoles, such as poly[2,2'(m-phenylene)-5,5'(6,6'benzimidazole)], polyozadiazoles, poly (n-phenyl triazoles), polybenzobenzimidazoles, polymides, poly(amide-imide), and polyether block amides (PEBAX)™.

In a preferred embodiment, the patch can be made of a flexible fabric which comprises an array of fibers. The fiber array includes woven and non-woven fabric structures. The fibers can have a diameter dimension between about 5 to 25 microns. In a preferred embodiment, the fiber is made of polyethylene terephthalate.

Metallic materials may be made into filaments and then woven to form a network of metal mesh suitable for making the patch. Polymer filaments may also be used together with the metallic filaments to form a network mesh.

Patches that are useful for the medical device of the present invention can be any biological patch. Biogenic tissue such as endoderm from the innermost layer of an artery (intima), collagen, fibrin, cellular matrix etc. may be used as therapeutic patches for the present invention. Biogenic macromolecules, also known as biopolymers, such as collagen, chitin, chitosan or cellulose including methylcellulose, ethylcellulose, hydromyethylcellulose, hydroxypropylcellulose, sodium carboxymethylcellulose, laminin, and hyaluronic acid may also be used to fabricate a biogenic patch.

The patch may comprise one or more sheets or films of a flexible material. In a preferred embodiment, the patch comprises a reservoir layer. The reservoir layer comprises a biologically active material which can replenish the supply of biologically active material once the initial release of the biologically active material has occurred. A preferred kind of patch includes a reservoir of angiogenic substance that leaches out from the inside of the patch, supplying more wound healing and angiogenic compound over time.

The patch may comprise one or more layers. In a preferred embodiment, the patch comprises an essentially impermeable layer, a matrix layer, and an adhesive layer. In another embodiment, the patch comprises an essentially impermeable layer, a matrix layer which is made up of a bioadhesive polymer. In a preferred embodiment, the patch comprises a biologically active material that is dispersed or embedded within a matrix layer of the patch. The impermeable layer is impermeable to the biologically active material such that the biologically active material that is present on one side of the patch will not be permeated to the opposing side of the patch.

The patch is preferably flexible and follows the contours of the surface of the body lumen and body cavity to be treated. The therapeutic patch can be of any shape and size depending on (1) the surface of the body lumen or body cavity that is to be treated and (2) whether it can be delivered to the body tissue by the medical device. In a preferred embodiment, the patch is circular.

The total thickness of the therapeutic patch can be about 10 microns to about 1 mm. Preferably, the thickness of the patch is about 50 microns to about 100 microns.

Optionally, the therapeutic patch can have a plurality of micro-needles disposed on the surface that comprises the adhesive material and biologically active material. The micro-needles are used to facilitate the delivery of the biologically active material to the surface of the body lumen, internal body cavity or organ. FIG. 2b illustrates a therapeutic patch having micro-needles that may be used in the present invention. The therapeutic patch 20 is similar to that of FIG. 2a except that on the surface that comprises the adhesive material and biologically active material, there are a plurality of micro-needles.

In one embodiment, the micro-needles that are disposed upon the surface of the patch are solid needles. When patch 20 is delivered to the surface of the body tissue, the solid micro-needles create nanoholes in the tissue. The biologically active material in the patch can then be delivered from the patch by capillary action along the outer surface of the micro-needles. The biologically active material seeps into the nanoholes where it is delivered to the body tissue.

When the micro-needles are non-hollow, i.e., solid, the micro-needles preferably have gutters on their exterior surface along their longitudinal axis. The biologically active material can travel along the gutter to the afflicted area by capillary action. A biologically active material is coated on the surface of the therapeutic patch and is forced into the nanoholes created by the micro-needles. Also, hollow microneedles and solid micro-needles can be used together on a single patch.

Alternatively, the micro-needles can be hollow and in liquid communication with a reservoir of a biologically active material, such as a reservoir layer of the therapeutic patch. The reservoir layer can be incorporated in the patch by any suitable means. In a preferred embodiment, the reservoir layer is attached to the therapeutic patch using a bioadhesive glue. The hollow micro-needles pierce the surface of the body lumen as the therapeutic patch is delivered to the surface of the body tissue. As the patch is pressed against the body tissue, the biologically active material is delivered to the body tissue through the hollow micro-needles from the reservoir.

Micro-needle devices and methods of manufacture are described in WO99/64580 or using microeletromechanical system (MEMS) technology. Micro-needles are generally construed as a needle of a diameter at most about 100 µm and of a length at most about 1 mm. An appropriate size of the micro-needles depends on the size of body lumen where the therapeutic patch is introduced and also the size of the biologically active material to be delivered. Generally, the outer diameter of the micro-needles is between about 10 nm and about 100 µm, preferably about 10 µm and below. The length of the micro-needles is typically between about 1 µm and about 1 mm, preferably about 10 µm and about 500 µm, more preferably between about 30 µm and about 200 µm. The minute size of the micro-needles will permit penetration at controllable depths minimizing tissue damages. Furthermore, the therapeutic patch can include micro-needles of different sizes, i.e., diameters and/or length.

The micro-needles of the present invention can be made from appropriate materials, such as metals, ceramics, semiconductors, organics, polymers and composites. Preferred materials are stainless steel, nickel, iron, tin, chromium, copper, gold, titanium, alloys of these or other metals, silicon, silicon dioxide and polymers, such as Polyethylene terephthalate (PET), polyurethane, Polyvinyl Chloride, polyamides, polycarbonates, polyethylene, and high-density ultra-high molecular weight polyethylene (UPE), Pebax™, Polylactic acid (PLA), polylactic acid-glycolic acid (PLGA), polycaprolactone-polylactic acid (PCL-PLA). Bioabsorbable polymers are referable in case the micro-needles are broken and left in a body lumen or tissue.

The micro-needles are micro-fabricated by processes known to artisans, e.g., etching techniques, such as photoresist, wet, and dry removal; electroplating and electroless plating; diffusion processes, such as boron, phosphorus, arsenic, and antimony diffusion; film deposition, such as evaporation, sputtering, chemical vapor deposition (CVD), epitaxy, electroplating, screen printing, lamination stereolithography, laser machining, and laser ablation; lithography; thermal oxidation of silicon. Those methods are explained in detail in PCT publication WO99/64580 and Micromechancial devices for Intravascular Drug Delivery, Michael L. Reed, Journal of Pharmaceutical Sciences, vol. 87, no. 11, (November 1998), 1387–1394, which are incorporated by reference.

The micro-needles may be solid or porous, and hollow or non-hollow. The term "porous" means having sufficient pores or voids where fluid and/or solid materials pass through. The hollow micro-needle may have a tip having an aperture connected to a lumen running through the micro-needle or a porous tip having a plurality of pores where at least one lumen running through the micro-needle is connected to one of the pores. The porous tips allow radial distribution of biologically active material from individual micro-needles.

The micro-needles are disposed on the surface of the therapeutic patch. The micro-needles can be oriented perpendicular or at an angle to the surface of the patch. The micro-needles may be distributed uniformly on the surface of the therapeutic patch which contacts the surface of the body lumen or organ when the patch is adhered to the surface of the body tissue. The number of micro-needles is not limited and depends on the targeted tissue. Generally, one micro-needle per ten (10) cells is preferred. Typically, the number of the micro-needles is more than about ten (10) per cm$^2$, preferably between about $1 \times 10^2$ and $1 \times 10^6$, more preferably between about $1 \times 10^3$ and $1 \times 10^5$ per cm$^2$. The numerous micro-needles ensure uniform delivery over the area of targeted tissue.

The therapeutic patch is disposed on the umbrella-like or basket-like expandable assembly. The patch is disposed in such a way that the surface that does not comprise the biologically active agent is preferably in contact with the wire elements of the umbrella-like or basket-like expandable assembly. In one embodiment, the patch is loosely wrapped or folded onto the wire elements like an accordion or in an S-shaped form similar to a collapsed balloon. In another embodiment, when the expandable assembly is in the expanded position, the patch is wrapped onto the wire elements. When the expandable assembly is changed to the retracted position, the wire elements fold the patch into a retracted position. In yet another embodiment, the patch is disposed upon he wire element using adhesive material such as a bioadhesive glue that dissolves when in contact with body fluid. In another embodiment, the patch has small holes at its periphery so that it may be disposed upon the wire element using hooks or securing elements that are disposed on the wire elements.

The opposing surface of the patch comprises a biologically active material and an adhesive material. Once deployed, the therapeutic patch can adhere onto he surface of a body lumen or an internal body cavity or organ using the adhesive material that is on the opposing surface of the patch. Suitable adhesive materials are described infra. Adhesive materials can be used to incorporate biologically active material into the patch and also to adhere the therapeutic patch onto the body tissue that is to be treated.

5.3 Applicable Biologically Active Materials

One can use the medical device of the present invention to deliver a biologically active material through a therapeutic patch to a surface of a body lumen or an internal body cavity or organ. The term "biologically active material" includes therapeutic agents, such as drugs, and also genetic materials and biological materials.

Suitable therapeutic agents include in general, antiplatelet agents, anti-coagulant agents, antimitotic agents, antioxidants, antimetabolite agents, and anti-inflammatory agents. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anticoagulant agents can include drugs such as protamine, hirudin and tick anticoagulant protein. Anti-cancer agents can include drugs such as taxol, and its analogs or derivatives antioxidant agents can include probucol, anti-proliferative agents can include drugs such as amlodipine and doxazosin. Antimitotic agents and antimetabolite agents can include drugs such as methotrexate, azathioprine, vincristine, vinblastine, 5-fluorouracil, adriamycin and mutamycin. Antibiotic agents can include penicillin, cefoxitin, oxacillin, tobramycin, and gentamycin.

Other examples of therapeutic agents that can be used in accordance with the present invention include, but are not limited to, anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as glucocorticoids, betamethasone, dexamethasone, prednisolone, corticosterone, budesonide, estrogen, sulfasalazine, and mesalamine; antineoplastic/ antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, antithrombin compounds, platelet receptor antagonists, anti-thrombin antibodies, anti-platelet receptor antibodies, aspirin, prostaglandin inhibitors, platelet inhibitors and tick antiplatelet peptides; vascular cell growth promoters such as growth factors, growth factor receptors, transcriptional activators, and translational promotors; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms.

The biologically active material can be used with any biologically non-active material including a solvent, a carrier or an excipient, such as sucrose acetate isobutyrate SABER™ (commercially available from SBS), ethanol, n-methyl pymolidone, dimethyl sulfoxide, benzyl benxoate and benze acetate.

Angiogenic substances, wound healing agents, and growth factors are suitable therapeutics that may be placed on the patch. Growth factors such as Fibroblast Growth Factor (FGF, FGF-1, FGF-2), Vascular Endothelial Growth Factors (VEGF) (all types including VEGF-2) and Endothelial Mitogenic Growth Factors are among the growth factors preferred for use with the present invention. Angiogenic substances such as estrogen, including estradiol (E2), estriol (E3) and 17-Beta Estradiol are also believed suitable for use with the present invention. Estrogen is believed to induce angiogenesis and increase permeability.

Genetic materials that are useful as biologically active material for the present invention include, for example, nucleic acid molecules such as DNA, RNA and other oligonucleotides having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides useful for the invention can also code for therapeutic polypeptides. A polypeptide is understood to be any translation product of a polynucleotide regardless of size, and whether glycosylated or not. Therapeutic polypeptides include as a primary example, those polypeptides that can compensate for a defective or deficient species in an animal, or those that act through degradation and regulation to limit or remove harmful cells from the body. In addition, the polypeptides or proteins that can be incorporated into the coating material of the present invention, or whose DNA can be incorporated, include without limitation, laminin, angiogenic factors including acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor; growth factors; cell cycle inhibitors, kinase ("TK") and other agents useful for interfering with cell proliferation, including agents for treating malignancies. Still other useful factors, which can be provided as polypeptides or as DNA encoding these polypeptides, include the family of bone morphogenic proteins ("BMP's"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. In addition, molecules capable of inducing an upstream or downstream effect of a BMP can be provided. Such molecules include any of the "hedgehog" proteins, or the DNAs encoding them.

Negatively charged biologically active materials that may be used as a biologically active material in the present invention can be any therapeutic agent that will associate with the positively charged moieties on the derivatized polymer at or below about a physiological pH, which is preferably about 7.4, and that will be substantially released therefrom at or above a physiological pH. Such negatively charged therapeutic agents include, but are not limited to nucleic acids such DNA, cDNA, RNA, antisense DNA or RNA, nucleotides, proteins, oligopeptides.

The genetic materials as described above may be inserted into a human body including viral vectors and non-viral vectors. Viral vectors include adenoviruses, gutted adenoviruses, adeno-associated virus, retroviruses, alpha virus (Semliki forest, Sindbis, etc.), lentiviruses, herpes simplex virus, replication competent viruses (e.g., ONYX-015), and hybrid vectors. Non-viral vectors include artificial chromosomes and mini-chromosomes, plasmid DNA vectors (e.g., pCOR), cationic polymers (e.g., polyethyleneimine, polyethyleneimine (PEI) graft copolymers (e.g., polyether-PEI and polyethylene oxide-PEI), neutral polymers Polyvinyl propylene, SP1017 (SUPRATEK) or other poloxamers composed of polyethylene oxide and polypropylene oxide, lipids or lipoplexes, nanoparticles and microparticles with and without targeting sequences such as the protein transduction domain (PDT).

The biological materials that may be used as biologically active material for the present invention include cells, yeasts, bacteria, proteins, peptides, cytokines and hormones. Suitable cells may be seeded onto the patch for delivery to various organs. Cells can be of human origin (autologous or allogeneic) or from an animal source (xenogeneic), genetically engineered, if desired, to deliver proteins of interest at the transplant site. The delivery media can be formulated as needed to maintain cell function and viability. Suitable cells include whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, macrophage, and satellite cells. Other types of cells may be suitable for seeding, for example, primary cultures of embryonal, neonatal, or adult cardiac tissue, cardiomyocytes, skeletal myoblasts. Cells that are suitable for a therapeutic application, more preferably after additional geneticengineering change, ex vivo modified cells (e.g., stem cells, fibroblasts, myoblasts, satellite cells, pericytes, cardimyocytes, skeletal myocytes, macrophage). Specifically, embryonal cardiac muscle cells are used for cell-mediated gene transfer, these cells can serve as a vesicle for a local gene transfer into the myocardium in particular for constructing healthy tissue and assisting contractile functions. For this purpose, the desired therapeutic genes are transfected by a viral gene transfer process, preferably with an adenovirus or an adenovirus-associated virus shuttle vector, or by a non-viral gene transfer process as described supra. Any type of graft may be placed on the patch, for example, allograft (same species donor and recipient) or homograft, as well as xenograft (different species donor and recipient) transplants. Applicable xenograft may be obtained from pigs, cows and sheep.

Drugs are suitable biologically active material that can be used in the present invention. Some drugs are employed to assist in treating problems associated with cardiac dilation. For example, digoxin increases the contractility of the cardiac muscle and thereby causes enhanced emptying of the dilated cardiac chambers. On the other hand, some drugs such as beta-blocking drugs decrease the contractility of the heart and therefore increase the likelihood of dilation. Other, pharmacological and/or biopharmaceutical treatments have been used previously. For example, angiotensin-converting enzyme (ACE) inhibitors, such as captopril and enalopril, have become standard therapy for patients with congestive heart failure. These drugs improve hemodynamic profile and exercise tolerance and reduce the incidence of morbidity and mortality in patients with congestive heart failure.

5.4 Methods of Incorporating Biologically Active Material into the Patch

The biologically active material can be of various physical states, e.g., molecular distribution, crystal forms or cluster forms. A biologically active material may be encapsulated by liposomes. Liposome comprising biologically active material useful in the present invention may be prepared in a number of ways known in the art. For example, microencapsulation techniques for the preparation of microcapsules having a wall or membrane of polymeric material are described in literature such as "Microencapsulation and Related Drug Processes" by P. D. Deasy, Marcel Dekker Inc. New York (1984).

Various methods may be used to incorporate biologically active material into the patch. For example, the biologically active material may be placed into the patch by absorption, adsorption, or chemical bonding such as covalent bonding. In another method, the biologically active material may be incorporated into a filament formed of various materials such as natural or synthetic polymers. The filament texture is preferably porous, mesh like. The filament with the biologically active material may be woven to form the patch. These patches may be cut into the appropriate shape depending on the surface of the body tissue being treated.

In a preferred method, the biologically active material is mixed with the polymer used to make the patch. The biologically active material can be embedded, dissolved or dispersed into the polymer solution used to make the patch.

A carrier may be used together with the biologically active material in a therapeutic patch. The carrier material will typically be one of two types. One type bioerodes rather uniformly over time, so that the bioerosion of the carrier is also the primary mechanism for releasing the biologically active material from a patch. The second type is a material which essentially remains intact during a substantial portion of the release period of the biologically active material. The mechanism of release of the biologically active material is by diffusion or other mechanism which does not require the carrier to be concurrently bioeroded. However, in such cases, shortly after the biologically active material has been depleted from the carrier, erosion of the patch should proceed in order to avoid the necessity of removing the therapeutic patch from the body tissue. Many carrier materials may be suitable for various embodiments of the medical device of the present invention. These carrier materials may be natural products, such as keratin, salol, triglycerides, fatty acids, lipids, latexes, as well as derivatives, salts of cellulose derivatives, alkaline or alkaline earth salts of cellulose acetate phthalate, ammonium salts of hydroxypropyl methyl cellulose phthalate, polysaccharide, synthetic polymers, such as, polyglycolic acid and derivatives of polyethylene glycol, polycaprolactone, polylactic acid, and copolymers thereof; materials such as starch, fatty alcohols, alginate polymers, albumin, calcium caseinate, calcium polypectate or gellan gum.

Carriers for the growth factors of the present invention include hydrogels. Other materials suitable for mixing with growth factors include: polyethylene oxide and its copolymers, polyvinylpyrolidone, polyacrylates, polyesters, gelatins, collagens, proteins, sodium alginate, karaya gum, guar gum, agar, algin, carrageenans, pectins, xanthan, starch based gums, hydroxyalkyl and ethyl ethers of cellulose, sodium carboxymethyl cellulose, polyvinyl alcohol, and hydrophilic polyurethanes.

The biologically active material may be glued onto the patch by means of a number of known synthetic, naturally-occurring or modified naturally-occurring substances which exhibit tackiness. These bioadhesive polymers and surgical adhesion polymers must be biocompatible, that is, nontoxic and/or inert, within the treated body tissue of a patient. The adhesive should also be compatible with the material forming the carrier, as well as the drug. In addition, the bioadhesive on the therapeutic patch is used to secure the patch on the surface of the body lumen or in internal body cavity or organ once the therapeutic patch is deployed. A variety of adhesives are suitable for the present invention, both for adhering a patch over the wall of a cavity to be treated, and for retaining biologically active material onto the patch. One adhesive is a hydrogel composed of gelatin and poly(L-glutamic acid) (PLGA). The hydrogel is formed by chemically cross linking gelatin and poly(L-glutamic acid). Another adhesive is fibrin glue. One suitable fibrin glue includes fibrinogen, thrombin, calcium chloride and factor VIII. Another family of adhesives is cyanoacrylates. Preferred cyanoacrylates include butyl-2-cyanoacrylate (Histoacryl), ethyl-2-cyanoacrylate, and octyl-2-cyanoacrylate. Gelatin-resorcinol formaldehyde-glutaraldehyde is another suitable adhesive. Others include carboxymethyl and hydroxypropyl methyl cellulose, and other cellulose derivatives; tragacanth, caraya, locust bean and other synthetic and natural gums such as algin, chitosan, starches, pectin, and naturally-occurring resins. In addition, many polymers having suitable adhesive properties can also be utilized, including without limitation: polyurethanes having amino groups, di- and tri-functional diols; polyvinyl acetates; polyamides; polyvinyl alcohols; polyvinyl pyrrolidone, polyacrylic acid; polystyrene; polylactides; polylactones; block co-polymers including polyesters, polyamides, and polyurethanes; and combinations and mixtures thereof. In a preferred embodiment, the opposing surface which comprises an adhesive material is coated with PEG.

In another embodiment, the biologically active material is applied onto the patch as a coating or layer. More than one coating of different biologically active material may be applied to the patch so that more than one biologically active material and/or carrier may be incorporated into the patch. The placement of the different layers may be determined by the diffusion or elution rates of the biologically active material involved as well as the desired rate of delivering the biologically active material to the body tissue. In another embodiment, the bottom-most coating layer contains a higher dose of a biologically active material and the subsequent coating layers contain a lower dose of a biologically active material. This gradient of biologically active material concentration provides replenishment of biologically active material from the first coating to the subsequent coatings, this allows the biologically active material to be released slowly over time.

In a preferred embodiment, the sustained delivery of the biologically active material will be for an extended period, longer than about three days and preferably, at least about one week. For treatment of the bladder, cancer, or other heart chronic conditions, it is preferred that the drug be delivered over a period up to about one month or more.

The concentration or loading of the biologically active material into or onto the therapeutic patch may be varied according to the therapeutic effects desired. Also, the loading, in terms of the ratio of biologically active material to carrier in the patch will depend upon the type of biologically active material and carrier used and the rate at which the biologically active material on the patch is released to the body tissue. Generally, the patch may contain 0.1–90% by weight or preferably 10–45% by weight of the biologically active material. Most preferably, 0.5–40% by weight of the drug should be incorporated in the patch.

5.5 Expandable Assembly Having An Umbrella-Like Configuration

Suitable umbrella-like expandable assemblies that may be employed by the present invention includes the umbrella catheters disclosed in U.S. Pat. Nos. 6,001,118; 6,053,932; 5,354,279 and 6,045,565.

Polymers that are useful for making umbrella-like expandable assemblies include biostable polymers, such as polyurethanes, silicones, and polyesters. Other polymers which can be used include polyolefins, polyamides, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, polycarbonates, acrylonitrile butadiene, styrene copolymers, ethylene vinyl-acetate, thermoplastic elastomers, ethylene-vinyl acetate copolymers, polyamides such as Nylon 6, 6 and polycaprolactone, alkyd resins, polycarbonates, polyoxymethylenes, polyimides, polyesters, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acidpolyethylene oxide copolymers.

The wire elements of the umbrella-like expandable assembly may be constructed of conductive metals having resilience and shape-retaining properties such as stainless steel, nickel-titanium alloys, spring steel alloys, and similar metals. Metallic materials include metals and alloys based on titanium (such as nitinol, nickel titanium alloys, thermo-memory alloy materials), platinum, tantalum, nickel-chrome, or cobalt-chromium (such as Elgiloy® and Phynox®) may be used to make the wire elements. Metallic materials also include clad composite filaments, such as those disclosed in WO 94/16646. Examples of ceramic materials include ceramics of alumina and glass-ceramics such as Macor®.

The wire elements may have circular or non-circular cross-sections. Preferably the wire elements are made from wires with circular diameters typically having a diameter in the range from about 0.1 mm to about 2 mm, preferably from about 0.2 mm to about 0.5 mm, and more preferably from about 0.2 mm to about 0.3 mm. Suitable wires with non-circular cross-sections should have cross-sectional areas equivalent to such wires having circular cross-sections. In a preferred embodiment, the wire elements may have hooks or attachment elements disposed thereon to secure a therapeutic patch. In one embodiment the hooks or attachment elements are at the distal ends of the wire elements.

In one embodiment, each wire element is configured and dimensioned such that each of the wire elements has equal length and that each of the wire element is equally spaced apart. The wire elements can diverge outwardly from the plunger or expansion mechanism in a uniform pattern, i.e., with the spacing between adjacent wire elements diverging in a substantially uniform and/or symmetric pattern. In other embodiments, the wire elements have different lengths and each of the wire element is unevenly spaced. Various other wire element divergence patterns, dimensions and configurations are also encompassed by the present invention.

The umbrella-like expandable assembly may be restrained within a protective sleeve which restrains the individual wire elements in a collapsed configuration to facilitate their introduction to the tissue target site. The protective sleeve can be a guide sheath being sized to slidably receive the elongated member and umbrella-like expandable assembly in its retracted position. When the guide sheath is removed, the umbrella-like expandable assembly expands.

In one embodiment, the medical device further comprises a penetrating element at the distal end of the elongated member. The penetrating element facilitates the passage of the medical device through thin membrane or organ walls to the site where treatment is needed. In one embodiment, the penetrating element is a pointed device made of metals or plastics. The penetrating element can be attached to or detached from the distal tip of the umbrella-like expandable assembly depending on whether such penetration is necessary for a particular treatment.

The medical device of the present invention is made by preparing a therapeutic patch and an expandable assembly of any configuration applicable. The expandable assembly is disposed upon the distal end of the elongated member and the therapeutic patch is disposed onto at least one wire element of the expandable assembly. The expandable assembly may be assembled separately first and then attached onto the distal end of the elongated member. Alternatively, the expandable assembly may be assembled on the elongated member. The medical device of the present invention can be made adaptable to catheters for delivery.

In one embodiment, the patch is disposed upon the wire element by loosely wrapping the patch on the wire elements of the expandable assembly of any configuration applicable. The patch may be wrapped onto the wire elements of the expandable assembly when the expandable assembly is in an expanded configuration. The expandable assembly may be retracted so that the wire elements fold the patch into a retracted position. In another embodiment, the patch may be wrapped onto the wire elements of the expandable assembly when the assembly is in a semi-expanded or a retracted configuration.

In one embodiment, the patch is attached to the wire element using a dissolvable adhesive material. After the patch is delivered to the treatment site, the adhesive material dissolves when it comes in contact with body fluid.

In another embodiment, the patch has holes on the periphery of the patch. Attachment elements disposed on the wire elements may secure the patch when the patch is in a retracted position. Once the patch expands, the patch is detached from the hooks and adheres to the surface of the tissue to be treated.

5.6 Expandable Assembly Having a Basket-Like Configuration

Basket-like expandable assemblies that may be used in the present invention can be any basket-like assembly for medical devices that are known in the art. Examples include U.S. Pat. No. 6,119,030; U.S. Pat. No. 5,725,525 and U.S. Pat. No. 5,647,870. Materials that are used to make the umbrella-like expandable assemblies can be used to make the basket-like expandable assembly.

In general, the basket-like expandable assembly is distally mounted on an elongated member such as a catheter body. The basket-like expandable assembly is formed by a plurality of wire elements. The basket-like expandable assembly includes at least three, generally flexible wire elements that radiate in a circumferentially spaced relationship. The wire elements are made of highly flexible metal alloy, e.g., nitinol, which has well known shape memory properties. In one embodiment, both ends of at least one wire element are secured to the distal end of the catheter. The wire elements are joined at their midpoint by a hub or a tip member. The wire elements are flexed into a three dimensional shape, e.g., such that each wire element forms a loop at the catheter's distal end. In general, the wire elements extend perpendicularly from the axis of the hub. The wire elements may be attached to the catheter's distal end in an evenly spaced relationship, aligned like the lines of longitude on a globe. The flexing of the wire elements creates a spheroid-like structure whose curvature approximates the curvature of the surface of an organ that the basket-like expandable assembly is to be applied to. In a preferred embodiment, the curvature of the spheroid-like structure created by the basket-like expandable assembly approximates that of the curvature of the endocardium. The structure presents a curved, uniform distal surface that follows the natural contour of the endocardial tissue. The assembly presents a surface essentially free of major projections that can extend into and damage endocardial tissue. Blunt tissue trauma is avoided. This geometry also makes it possible to place biologically active material delivery system, in this case a patch, into intimate contact with the endocardial tissue.

In a preferred embodiment, each wire element of the basket-like expandable assembly includes a region of reduced width and/or thickness near the hub. Thinning of the width of the wire elements in this region presents a compact geometry that accommodates the collapsing of multiple, closely spaced wire elements. Reducing the thickness of the wire elements in this region imparts greater flexibility to the wire elements. The localized reductions of width and/or thickness also reduces force required to flex the structure inward into a collapsed condition.

The medical device comprising a self-expanding basket-like expandable assembly may include a guide sheath slidable along the catheter body in one direction to collapse the basket-like expandable assembly for introduction into the patient's body. The sheath slides along the catheter in another direction to deploy the self-expanding basket-like expandable assembly within the patient's body. After deployment and placement of therapeutic patch onto the surface of the treated lumen, the basket-like expandable assembly is collapsed again as described and retrieved from the body.

In one embodiment, the medical device further comprises a penetrating element at the tip of the basket-like expandable assembly.

In another embodiment, the first end of the wire element is attached to the distal end of the elongated member and the other end of the wire element is attached to a hub which is at a point more distal than the first end of the wire element.

The basket-like expandable assembly may be non-self-expandable. In one embodiment, the basket-like expandable assembly comprises an expansion mechanism similar to that of the umbrella-like expandable assembly. In another embodiment, the expansion mechanism is a plunger being sized to slidably receive a portion of the elongated member. Also, a first end of at least one wire element can be flexibly connected to the plunger. The other end of the wire element is attached to a hub at a point more distal than the first end of the wire element. When the plunger moves distally along the elongated member, the wire elements are flexed into a basket-like configuration.

5.7 Uses for the Invention

The device of the present invention can be used to apply the biologically active material to any surface of a body lumen where a catheter can be inserted. Such body lumen include, without limitation, heart chambers, blood vessels, urinary tract, coronary vasculature, esophagus, trachea, colon, and biliary tract. Various organs can be treated using the medical device of the invention, without limitation, the bladder, lungs, spleen, liver, eyes, uterus and intestines. There are ways by which the medical device of the invention may be used to treat the surface of a body lumen or internal body cavity or organ, for example, through surface deployment (i.e., intrapericardial attachment) or transmyocardial patch depolyment. First, the therapeutic patch can deliver a biologically active material to the surface of a body lumen or cavity for treatment. This type of patch is preferably biodegradable since once the delivery of biologically active material is complete, the patch is no longer needed. It is preferable that the patch is biodegradable so that further steps of removing it from the body lumen or cavity would not be necessary. Second, the therapeutic patch delivers a biologically active material to the surface of a body lumen or internal cavity or organ for treatment and at the same time, the patch is necessary to hold the surface of the body lumen or internal cavity or organ in place or act as a permanent barrier to repair a defect or a lesion. This type of patch is preferably non-biodegradable since the patch is needed for permanent support.

The method of the present invention may be used to treat various diseases, for example, bladder cancer, congestive heart failure, ulcers, cardiomyopathy and congenital defects of the heart. For the treatment of heart diseases, various types of drugs that are suitable for treating cardiac diseases such as digoxin, beta-blockers, ACE inhibitors may be used as discussed supra. Other biologically active material can be applied within the heart chamber walls, external heart wounds, or incorporated into the heart myocardium, such as the myocardium, pericardium, endocardium and epicardium.

Some of the more common types of congenital cardiac defects that may be treated using the medical device of the present invention include atrial septal defect (ASD), ventricular septal defect (VSD), and patent ductus arteriosis (PDA). An ASD is a hole in the cardiac septum between the left and right atria, while a VSD is a hole in the septum between the left and right ventricles. Patent ductus arteriosis is incomplete closure of the opening between the pulmonary artery and the aorta that is present during fetal development. These conditions may cause blood to abnormally shunt from the right side of the heart to the left side of the heart without being properly oxygenated in the lungs. This results in deprivation of oxygen to the body tissues. In addition, blood in the left side of the heart may shunt back to the right side through the defect rather than being pumped into the arterial system, causing abnormal enlargement of the right chambers of the heart.

Another use for the method of the present invention is to treat cardiac ruptures. Cardiac rupture refers to a rupture of the left ventricle of the heart, generally following an acute myocardial infarction. If untreated, the condition usually is fatal immediately or within a few days depending on the extent of the rupture. It is believed that such rupture occurs in approximately 10% of patients with fatal acute myocardial infarction. Bates et al., 1997 Am. J. Cardiol. 40: 429–437. It causes 25,000 deaths a year in the United States alone and is the second most common cause of the death after an acute myocardial infarction. The above mentioned defects may be treated by using the medical device of the present invention by delivering a therapeutic patch to repair the defect.

The method of treatment of the invention comprises the steps of inserting the medical device of the present invention into the patient's body in a manner where the patch of the medical device is adjacent to the body tissue surface being treated. The medical device comprises an elongated member such as a guidewire or a catheter, either an umbrella-like expandable assembly or a basket-like expandable assembly; and a patch which is generally a therapeutic patch. The medical device is deployed by expanding the umbrella-like or basket-like expandable assembly. Upon expansion of the umbrella-like or basket-like expandable assembly, the therapeutic patch adheres to the surface of a body tissue to be treated. The umbrella-like or basket-like expandable assembly is retracted to its collapsed position and the medical device removed from the body of the patient.

When the medical device with an umbrella-like expandable assembly reaches the surface of the body tissue that needs treatment, the umbrella-like expandable assembly is deployed and the wire elements extend away from the elongated member. The therapeutic patch, which is disposed on the wire elements of the umbrella-like expandable assembly unfolds as the umbrella-like expandable assembly is deployed. The wire elements of the umbrella-like expandable assembly is then used to apply a mild pressure to the patch, allowing close approximation of the patch onto the surface of the body tissue. The side of the patch which is loaded with an adhesive material secures the patch onto the surface of the body lumen or internal cavity or organ. The entire patch is attached to the surface of the body tissue to be treated.

In a preferred embodiment, a medical device with an umbrella-like expandable assembly is used to apply a therapeutic patch onto the internal surface of the left ventricle of the heart. In a minimally invasive procedure, the medical device can be delivered through the lumen of a delivery catheter or a thoracoscope to a heart chamber. The medical device with an umbrella-like expandable assembly can be introduced into the left ventricle of the heart via the aorta using a femoral, trachial or carotid artery approach. In a specific embodiment, the medical device may be advanced to the desired location in the body using a position controllable tip that can be remotely manipulated from outside the patient in a manner similar to an ordinary gastroendoscope.

In a healthy heart, the wall muscle of the heart is normally approximately 10 mm in thickness. In a diseased heart, the wall muscle of the heart can be much thicker (hypertrophic) or much thinner (dilated myopathy).

In one embodiment, the medical device with an umbrella-like expandable assembly is used to apply a therapeutic patch on the outside surface of the heart. This is known as transmyocardial patch deployment. After the medical device is advanced to the left ventricle using the method discussed above, an optional penetrating device installed at the tip of the medical device is inserted approximately 1–4 mm into the myocardium. The tip of the medical device is advanced through the pericardial sac to within a few millimeters of the site that requires treatment. The therapeutic patch is introduced to the external surface of the heart as the tip pushes through the myocardium.

In another embodiment, the medial device does not go through the pericardium. The therapeutic patch is delivered to the surface of the heart (epicardium) which is between the heart and pericardium. This is known as intrapericardial patch development. (See U.S. Pat. Nos. 5,997,525; 5,840,059; 5,797,870.) The patch can be applied to the epicardium using a mini-thoracotomy.

In another embodiment, a medical device with a basket-like expandable assembly is used to apply a therapeutic patch onto the surface of the endocardium. Initially, the therapeutic patch that is disposed on the wire elements of the basket-like expandable assembly is compressed into a retracted condition. The basket-like expandable assembly that is disposed on the distal end of a catheter body is moved through a guide sheath for introduction into a patient's body through the cardiovascular system. The basket-like expandable assembly and the therapeutic patch are deployed at a target site within a heart chamber, where the guide sheath is pulled back, allowing the wire elements of the basket-like expandable assembly to return to their expanded condition. The therapeutic patch expands and using minor pressure, the therapeutic patch is then secured onto the endocardium of the heart chamber.

Whereas the invention has been shown and described in connection with specific embodiments hereof, many modifications, substitutions and additions may be made which are within the intended broad scope of the appended claims. Thus, it should be understood that the present invention encompasses the use of other methods and medical devices for delivery a therapeutic patch to the body tissue of a patient. Those skilled in the art will recognize, or be able to ascertain using no more than routine experimentation, many equivalents to the specific embodiments of the invention described herein. Indeed, various modifications of the invention in addition to those described herein will become apparent to those skilled in the art from the foregoing description and accompanying figures. Such equivalents are intended to be within the scope of the following claims.

All publications, patents and patent applications mentioned in this specification are herein incorporated by reference into the specification to the same extent as if each individual publication, patent or patent application was specifically and individually indicated to be incorporated herein by reference.

What is claimed:

1. A medical device for treating body tissue of a patient comprising:
   (a) an elongated member having a proximal end and a distal end;
   (b) an expandable assembly disposed at the distal end of the elongated member, wherein the expandable assembly is capable of changing from a retracted position to an expanded position and the expandable assembly comprises a plurality of wire elements and wherein each wire element has a first end and a second end; and
   (c) a patch having two opposing surfaces; wherein one of the opposing surfaces comprises an adhesive material and a biologically active material; wherein the other opposing surface is disposed upon at least one of the wire elements, and wherein the wire elements are arranged in a basket-like configuration when the expandable assembly is in the expanded position and wherein both ends of at least one wire element is connected to the distal end of the elongated member.

2. The medical device of claim 1 wherein at least two wire elements have midpoints between the ends of the wire elements and wherein the medical device further comprises a hub which connects the midpoints.

3. The medical device of claim 1 which further comprises a sheath being sized to slidably receive the elongated member and expandable assembly in its retracted position.

4. The medical device of claim 1 which further comprises an expansion mechanism for expanding the expandable assembly.

5. The medical device of claim 1 wherein the expandable assembly comprises about three or more wire elements.

6. The medical device of claim 5 wherein the expandable assembly comprises up to about twenty wire elements.

7. The medical device of claim 1 wherein each of the wire elements are of approximately equal lengths.

8. The medical device of claim 1 wherein each of the wire elements are approximately evenly spaced.

9. The medical device of claim 1 wherein the patch comprises a material selected from the group consisting of natural polymers, synthetic polymers, metals and biological fabric.

10. The medical device of claim 1 wherein the patch is circular in shape.

11. The medical device of claim 1 wherein the thickness of the patch is about 10 micron to about 1 mm.

12. The medical device of claim 1 wherein one side of the patch is substantially impermeable.

13. The medical device of claim 1 wherein the biologically active material comprises at least one of cells, genetic materials or drugs.

14. The medical device of claim 13 wherein the cells comprise at least one of endothelial progenitor cells, stem cells, cardiomyocytes, skeletal myoblasts or transformed cells.

15. The medical device of claim 13 wherein the genetic materials are nucleic acid molecules encoding proteins comprising at least one of FGF, FGF-1, FGF-2, EMGF or VEGF.

16. The medical device of claim 13 wherein the drugs comprise at least one of estrogen, estradiol, estriol, dioxin, captopril or enalopril.

17. The medical device of claim 1 wherein the opposing surface of the patch which comprises an adhesive material further comprises carbowax.

18. The medical device of claim 1 wherein the adhesive material is a bioadhesive material comprising at least one of hydrogels, fibrin glue, cyanoacrylates, gelatin-resorcinol formaldehyde-glutaraldehyde, synthetic gums or natural gums.

19. A medical device for treating body tissue of a patient comprising:
   (a) an elongated member having a proximal end and a distal end:
   (b) an expandable assembly disposed at and connected to the distal end of the elongated member, wherein the expandable assembly is capable of changing from a retracted position to an expanded position and the expandable assembly comprises a plurality of wire elements and wherein each wire element has a first end and a second end; and
   (c) a patch having two opposing surfaces; wherein one of the opposing surfaces comprises an adhesive material and a biologically active material; wherein the other opposing surface is disposed upon at least one of the wire elements; and wherein the wire elements are arranged in a basket-like configuration when the expandable assembly is in the expanded position and the first end of the wire element is connected to the distal end of the elongated member and the second end of the wire is connected to the elongated member at a point more proximal than the first end of the wire element.

20. A medical device for treating body tissue of a patient comprising:
   (a) an elongated member having a proximal end and a distal end;
   (b) an expandable assembly disposed at and connected to the distal end of the elongated member, wherein the expandable assembly is capable of changing from a retracted position to an expanded position and the expandable assembly comprises a plurality of wire elements and wherein each wire element has a first end and a second end; and
   (c) a patch having two opposing surfaces; wherein one of the opposing surfaces comprises an adhesive material and a biologically active material; wherein the other opposing surface is disposed upon at least one of the wire elements, and wherein a penetrating element is disposed at the distal end of the elongated member.

21. The medical device of claim 20 wherein the wire elements are arranged in a basket-like configuration when the expandable assembly is in the expanded position and at least one end of at least one wire element is connected to the distal end of the elongated member.

* * * * *